United States Patent
Srinivasan et al.

(10) Patent No.: US 11,020,143 B2
(45) Date of Patent: Jun. 1, 2021

(54) ADAPTIVE STEERING ADJUSTMENT FOR NEEDLE VISUALIZATION

(71) Applicant: EDAN INSTRUMENTS, INC., Shenzhen (CN)

(72) Inventors: Seshadri Srinivasan, Sunnyvale, CA (US); Ling Feng, Shenzhen (CN)

(73) Assignee: EDAN INSTRUMENTS, INC., Shenzhen (CN)

( * ) Notice: Subject to any disclaimer, the term of this patent is extended or adjusted under 35 U.S.C. 154(b) by 636 days.

(21) Appl. No.: 15/214,072

(22) Filed: Jul. 19, 2016

(65) Prior Publication Data

US 2017/0020559 A1    Jan. 26, 2017

Related U.S. Application Data

(60) Provisional application No. 62/194,727, filed on Jul. 20, 2015.

(51) Int. Cl.
| | | |
|---|---|---|
| A61B 17/34 | (2006.01) | |
| A61B 8/08 | (2006.01) | |
| A61B 8/14 | (2006.01) | |
| G01S 7/52 | (2006.01) | |
| A61B 8/00 | (2006.01) | |
| A61B 90/00 | (2016.01) | |

(52) U.S. Cl.
CPC ........ *A61B 17/3403* (2013.01); *A61B 8/0833* (2013.01); *A61B 8/0841* (2013.01); *A61B 8/145* (2013.01); *A61B 8/5207* (2013.01); *A61B 8/5223* (2013.01); *A61B 8/54* (2013.01); *G01S 7/52085* (2013.01); *A61B 2017/3413* (2013.01); *A61B 2090/378* (2016.02); *A61B 2090/3925* (2016.02)

(58) Field of Classification Search
CPC . A61B 17/3403; A61B 8/0833; A61B 8/0841; A61B 8/145; A61B 8/5207; A61B 8/5223; A61B 8/54; A61B 2090/378; A61B 2090/3925; A61B 2017/3413; G01S 7/52085
See application file for complete search history.

(56) References Cited

U.S. PATENT DOCUMENTS

| | | | | |
|---|---|---|---|---|
| 5,971,928 A | * | 10/1999 | Dodd | G01S 7/52026 600/458 |
| 6,221,016 B1 | * | 4/2001 | Hayakawa | A61B 8/0833 600/443 |

(Continued)

*Primary Examiner* — Amelie R Davis
*Assistant Examiner* — John Denny Li

(57) ABSTRACT

A steering adjustment for a needle visualization ultrasound system includes a needle, an ultrasound interface and one or more processing electronics. The ultrasound interface receives ultrasound imaging information from a first set of ultrasound firings. The processing electronics are coupled to the ultrasound interface. The processing electronics utilize the information from the first set of firings and identify the angle of the needle and the optimized steering frame angle. The processing electronics are further configured to cause a second set of firings. The second set of firings are configured for the identified needle angle and steering frame angle. The processing electronics are further configured to utilize the ultrasound information from the second set of firings to adaptively and dynamically enhance the visualization of the needle.

18 Claims, 9 Drawing Sheets

(56) References Cited

U.S. PATENT DOCUMENTS

| | | | |
|---|---|---|---|
| 8,348,848 B1* | 1/2013 | Tamura | A61B 8/0841 600/441 |
| 2002/0173719 A1* | 11/2002 | Zhao | A61B 8/0833 600/437 |
| 2005/0101867 A1* | 5/2005 | Johnson | A61B 8/14 600/459 |
| 2007/0173722 A1* | 7/2007 | Ustuner | A61B 8/5269 600/443 |
| 2011/0112549 A1* | 5/2011 | Neubach | A61B 8/485 606/130 |
| 2012/0209107 A1* | 8/2012 | Guo | A61B 8/0841 600/424 |
| 2013/0096430 A1* | 4/2013 | Yoshiara | A61B 8/0841 600/438 |
| 2015/0297092 A1* | 10/2015 | Irisawa | A61B 8/12 600/407 |

* cited by examiner

ADAPTIVE STEERING ADJUSTMENT FOR NEEDLE VISUALIZATION

CROSS-REFERENCE TO RELATED APPLICATION

This application claims priority from U.S. Provisional Patent Application No. 62/194,727, filed Jul. 20, 2015. The contents of this application is incorporated herein by reference in its entirety.

BACKGROUND

The present disclosure relates generally to ultrasound systems that include processing electronics and needles. More specifically, the present disclosure relates to an angle processor that computes a needle angle and steering frame angle for adaptive enhanced needle visualization.

Conventional ultrasound systems use a fixed number of steered frames for visualizing a needle. The number and extent of the steering frames determine the efficacy of needle visualization. A large number of steering frames and a larger angular extent ensure that the needle is visualized adequately. However, large steering angles result in higher grating lobes and high numbers of steering frames lower the frame-rate. Systems typically trade-off the number of steering frames with the angle of steering frames for needle visualization.

The inventors of the present disclosure have recognized that dynamically and adaptively determining the angle of the needle and thereby reducing the number of steering frames improves the intensity of the needle and the frame-rate. The number and angles of the steered frames are automatically and dynamically updated to provide benefits of better needle visualization, which can be crucial for accurate needle placement.

SUMMARY

One implementation of the present disclosure relates to a steering adjustment for a needle visualization ultrasound system including a needle, an ultrasound interface that receives ultrasound imaging information from a first set of firings and processing electronics coupled to the ultrasound interface and configured to utilize the ultrasound imaging information from the first set of firings to identify a first needle angle and a first steering frame angle. The processing electronics are further configured to cause a second set of firings to be configured for the identified first needle angle and first steering frame angle and utilize the ultrasound imaging information from the second set of firings.

In some embodiments, the processing electronics are configured to make the first set of firings sparse firings.

In some embodiments, the processing electronics are configured to begin the first set of firings based on an event.

In some embodiments, the processing electronics are configured to make the second set of firings dense firings.

In some embodiments, the processing electronics identify the needle angle by subtracting a tissue frame from the steered frames.

In some embodiments, the processing electronics identify the needle angle by removing grating lobes through edge detection processing.

In some embodiments, the processing electronics identify the needle angle using statistical functions.

In some embodiments, the processing electronics identify the needle angle using image transformations.

In some embodiments, the processing electronics identify the steering frame angle by identifying the steered frame with the highest energy.

In some embodiments, the processing electronics change the steering frame dynamically and adaptively to accommodate changes in the needle angle to enhance needle visualization.

In some embodiments, the change of the steering frame is made periodically.

In some embodiments, the change of the steering frame is made continuous.

In some embodiments, the second set of firings do not occur until a set time interval is reached.

Another implementation of the present disclosure is an ultrasound machine. The ultrasound machine includes an ultrasound interface that receives ultrasound imaging information from multiple sets of firings to obtain steered frames and processing electronics coupled to the ultrasound interface and configured to utilize the ultrasound imaging information from the multiple sets of firings to identify the angle of a needle dynamically and adaptively.

Another implementation of the present disclosure is a method of steering adjustment for needle visualization. The steps of the method include receiving ultrasound imaging data from a first set of firings, identifying a first needle angle, determining a first steering angle, receiving ultrasound imaging data from a second set of firings, processing the imaging data from the second set of firings, and adaptively and dynamically repeating the method to accommodate for changes in the needle angle.

In some embodiments, the first set of firings are sparse firings.

In some embodiments, the second set of firings are dense firings.

In some embodiments, identifying the needle angle involves subtracting a tissue frame from the steered frames.

In some embodiments, identifying the needle angle involves removing grating lobes through edge detection processing.

In some embodiments, identifying the needle angle involves using statistical functions.

In some embodiments, identifying the needle angle involves using image transformations.

DETAILED DESCRIPTION

Referring generally to the FIGURES, systems and methods for adaptive steering adjustment are shown, according to various exemplary embodiments. The systems and methods described herein may be used to adaptively enhance needle visualization in an imaging system. For example, the adaptive steering adjustment may include a first set of firings, a first needle angle and frame angle computation and a second set of firings.

The present disclosure generally relates to systems and methods for adaptively enhancing needle visualization in an ultrasound system using adaptive steering frame adjustment. An angle processor is used as an example in the various figures to help illustrate the present disclosure. However, it should be recognized that the present disclosure can be applied to a wide variety of processing electronics and other electronic devices that process imaging data.

In one embodiment of the present disclosure, an ultrasound system includes an angle processor configured to compute the angle of the needle, and steering frame angles. The processing electronics can be configured to repeat the process periodically, continuously, or based on another user defined time interval. The processing electronics may be configured to transmit coarse firing for the first firing set. The processing electronics may be further configured to transmit dense firing for the first firing set. In one embodiment, the first set of firings as triggered by an event (e.g. needle entrance). The needle visualization would then be enhanced, resulting in ultrasound images with a more accurate display of needle placement.

Figure 1A:
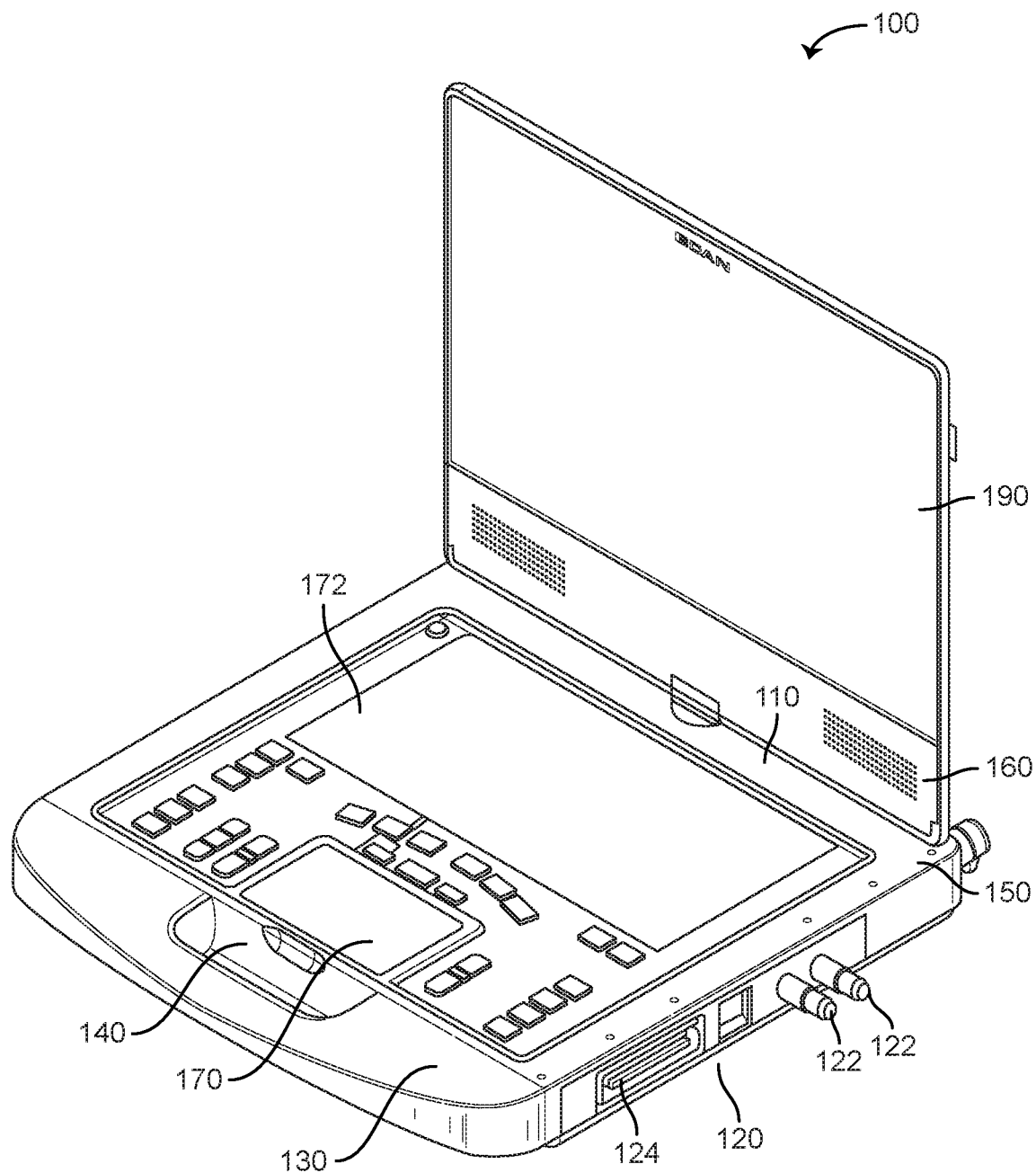
FIG. 1A is a drawing of a portable ultrasound system, according to an exemplary embodiment.

Referring now to FIG. 1A, one embodiment of portable ultrasound system 100 is illustrated. Portable ultrasound system 100 may include display support system 110 for increasing the durability of the display system. Portable ultrasound system 100 may further include locking lever system 120 for securing ultrasound probes and/or transducers. Some embodiments of portable ultrasound system 100 include ergonomic handle system 130 for increasing portability and usability. Further embodiments include status indicator system 140 which displays, to a user, information relevant to portable ultrasound system 100. Portable ultrasound system 100 may further include features such as an easy to operate and customizable user interface, adjustable feet, a backup battery, modular construction, cooling systems, etc.

Still referring to FIG. 1A, main housing 150 houses components of portable ultrasound system 100. In some embodiments, the components housed within main housing 150 include locking lever system 120, ergonomic handle system 130, and status indicator system 140. Main housing 150 may also be configured to support electronics modules which may be replaced and/or upgraded due to the modular construction of portable ultrasound system 100. In some embodiments, portable ultrasound system 100 includes display housing 160. Display housing 160 may include display support system 110. In some embodiments, portable ultrasound system 100 includes touchpad 170 for receiving user inputs and displaying information, touchscreen 172 for receiving user inputs and displaying information, and main screen 190 for displaying information.

Figure 1B:
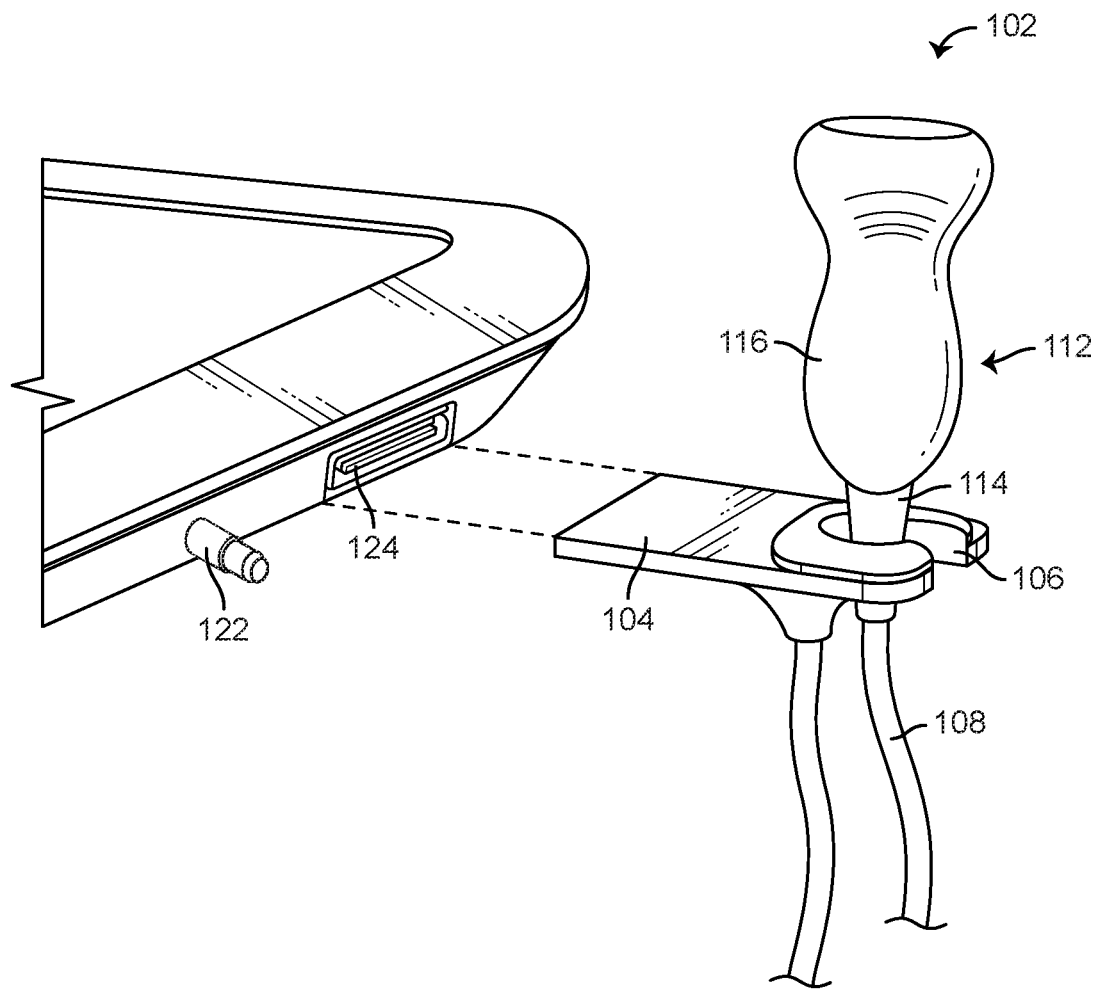
FIG. 1B is a drawing of an ultrasound transducer assembly for coupling to the portable ultrasound system of FIG. 1A, according to an exemplary embodiment.

Referring now to FIG. 1B, ultrasound transducer assembly 102 is shown. According to an exemplary embodiment, ultrasound transducer assembly 102 includes a connection assembly to pin (122) or socket (124) type ultrasound interface, shown as ultrasound interface connector 104, coupled to cable 108. Cable 108 may be coupled to a transducer probe 112. While FIG. 1B shows only one transducer assembly 102, more transducer assemblies may be coupled to the ultrasound system 100 based on the quantity of pin (122) or socket (124) type ultrasound interfaces.

Ultrasound interface connector 104 is movable between a removed position with respect to pin (122) or socket (124) type ultrasound interface, in which ultrasound interface connector 104 is not received by pin (122) or socket (124) type ultrasound interface, a partially connected position, in which ultrasound interface connector 104 is partially received by pin (122) or socket (124) type ultrasound interface, and a fully engaged position, in which ultrasound interface connector 104 is fully received by pin (122) or socket (124) type ultrasound interface in a manner that electrically couples transducer probe 112 to ultrasound system 100. In an exemplary embodiment, pin (122) or socket (124) type ultrasound interface may include a sensor or switch that detects the presence of the ultrasound interface connector 104.

In various exemplary embodiments contained herein, the ultrasound interface connector 104 may house passive or active electronic circuits for affecting the performance of the connected transducers. For example, in some embodiments the transducer assembly 102 may include filtering circuitry, processing circuitry, amplifiers, transformers, capacitors, batteries, failsafe circuits, or other electronics which may customize or facilitate the performance of the transducer and/or the overall ultrasound machine. In an exemplary embodiment, ultrasound interface connector 104 may include a bracket 106, where the transducer probe 112 may be stored when not in use.

Transducer probe 112 transmits and receives ultrasound signals that interact with the patient during the diagnostic ultrasound examination. The transducer probe 112 includes a first end 114 and a second end 116. The first end 114 of the transducer probe 112 may be coupled to cable 108. The first end 114 of the transducer probe 112 may vary in shape to properly facilitate the cable 108 and the second end 116. The second end 116 of the transducer probe 112 may vary in shape and size to facilitate the conduction of different types of ultrasound examinations. These first end 114 and second end 116 of transducer probe 112 variations may allow for better examination methods (e.g., contact, position, location, etc.).

A user (e.g., a sonographer, an ultrasound technologist, etc.) may remove a transducer probe 112 from a bracket 106 located on ultrasound interface connector 104, position transducer probe 112, and interact with main screen 190 to conduct the diagnostic ultrasound examination. Conducting the diagnostic ultrasound examination may include pressing transducer probe 112 against the patient's body or placing a variation of transducer probe 112 into the patient. The ultrasound image acquired may be viewed on the main screen 190.

Figure 1C:
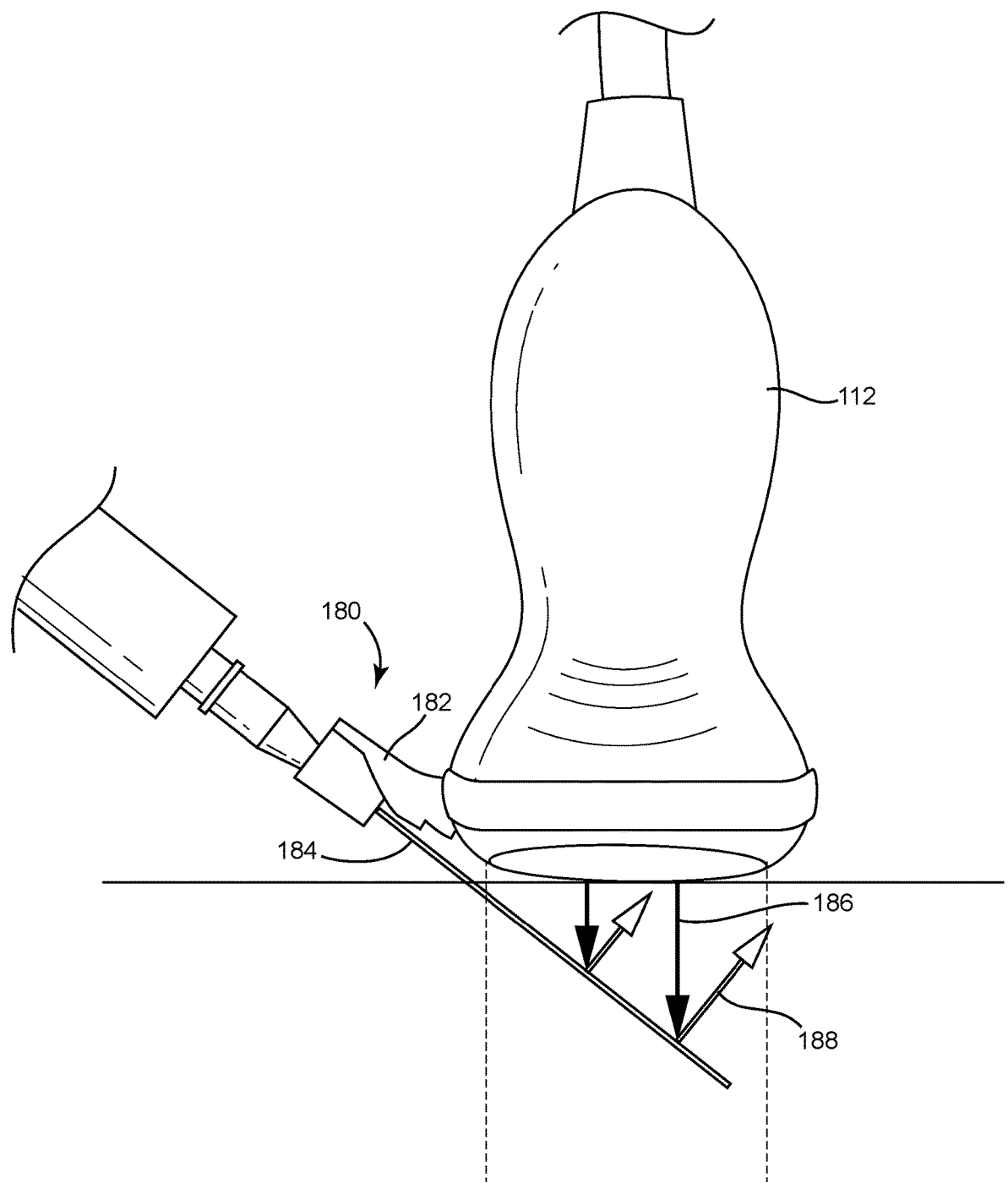
FIG. 1C is a drawing of the ultrasound probe from FIG. 1B, coupled to a needle assembly, according to an exemplary embodiment.

FIG. 1C is a drawing of the ultrasound probe 112 from FIG. 1B, coupled to a needle assembly 180, according to an exemplary embodiment. Needle assembly 180 includes needle mounting device 182, and a needle 184. Needle mounting device 182 may be coupled to the probe 112. In another embodiment, needle mounting device 182 is a separate component. In some embodiments, needle mounting device 182 is adjustable. In other embodiments, needle mounting device 182 maintains a fixed position. Needle mounting device 182 may be coupled to needle 184. In other embodiments, mounting device 182 is not coupled to needle 184. In another embodiment, needle 184 is removable from mounting device 182. Needle 184 may be a straight needle. In other embodiments, needle 184 is nonlinear. In some embodiments, needle 184 is a standard medical needle. In other embodiments, needle 184 is an echogenic needle, made specifically for enhanced viewing with ultrasound systems. Transducer probe 112 may transmit the incident sound beams 186. In an exemplary embodiment, transducer probe 112 has steering frames and can vary the transmitted sound signals transmitted from single steering frames. The angle of needle 184 may cause the sound beams 186 to be reflected as reflected sound beams 188. Depending on the angle of the sound beams 186, the reflected sound beams 188 may or may not reflect back to hit the transducer probe.

Figure 2:
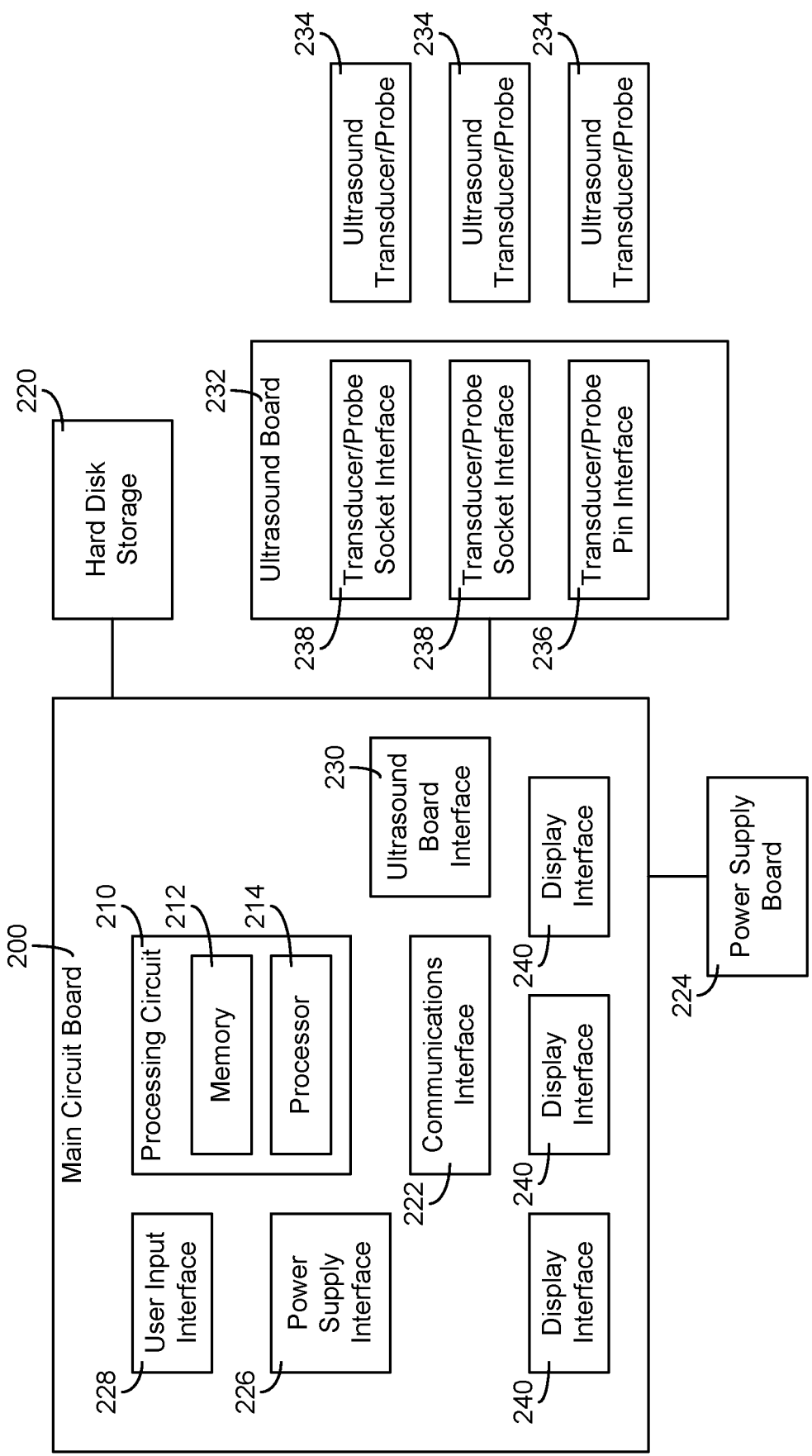
FIG. 2 is a block diagram illustrating components of one embodiment of a portable ultrasound system.

Referring to FIG. 2, a block diagram shows internal components of one embodiment of portable ultrasound system 100. Portable ultrasound system 100 includes main circuit board 200. Main circuit board 200 carries out computing tasks to support the functions of portable ultrasound system 100 and provides connection and communication between various components of portable ultrasound system 100. In some embodiments, main circuit board 200 is configured so as to be a replaceable and/or upgradable module.

To perform computational, control, and/or communication tasks, main circuit board 200 includes processing circuit 210. Processing circuit 210 is configured to perform general processing and to perform processing and computational tasks associated with specific functions of portable ultrasound system 100. For example, processing circuit 210 may perform calculations and/or operations related to producing an image from signals and or data provided by ultrasound equipment, running an operating system for portable ultrasound system 100, receiving user inputs, etc. Processing circuit 210 may include memory 212 and processor 214 for use in processing tasks. For example, processing circuit 210 may perform calculations and/or operations.

Processor 214 may be, or may include, one or more microprocessors, application specific integrated circuits (ASICs), circuits containing one or more processing components, a group of distributed processing components, circuitry for supporting a microprocessor, or other hardware configured for processing. Processor 214 is configured to execute computer code. The computer code may be stored in memory 212 to complete and facilitate the activities described herein with respect to portable ultrasound system 100. In other embodiments, the computer code may be retrieved and provided to processor 214 from hard disk storage 220 or communications interface 222 (e.g., the computer code may be provided from a source external to main circuit board 200).

Memory 212 may be any volatile or non-volatile computer-readable storage medium capable of storing data or computer code relating to the activities described herein. For example, memory 212 may include modules which are computer code modules (e.g., executable code, object code, source code, script code, machine code, etc.) configured for execution by processor 214. Memory 212 may include computer executable code related to functions including ultrasound imagining, battery management, handling user inputs, displaying data, transmitting and receiving data using a wireless communication device, etc. In some embodiments, processing circuit 210 may represent a collection of multiple processing devices (e.g., multiple processors, etc.). In such cases, processor 214 represents the collective processors of the devices and memory 212 represents the collective storage devices of the devices. When executed by processor 214, processing circuit 210 is configured to complete the activities described herein as associated with portable ultrasound system 100.

Hard disk storage 220 may be a part of memory 212 and/or used for non-volatile long term storage in portable ultrasound system 100. Hard disk storage 220 may store local files, temporary files, ultrasound images, patient data, an operating system, executable code, and any other data for supporting the activities of portable ultrasound device 100 described herein. In some embodiments, hard disk storage 220 is embedded on main circuit board 200. In other embodiments, hard disk storage 220 is located remote from main circuit board 200 and coupled thereto to allow for the transfer of data, electrical power, and/or control signals. Hard disk storage 220 may be an optical drive, magnetic drive, a solid state hard drive, flash memory, etc.

In some embodiments, main circuit board 200 includes communications interface 222. Communications interface 222 may include connections which enable communication between components of main circuit board 200 and communications hardware. For example, communications interface 222 may provide a connection between main circuit board 200 and a network device (e.g., a network card, a wireless transmitter/receiver, etc.). In further embodiments, communications interface 222 may include additional circuitry to support the functionality of attached communications hardware or to facilitate the transfer of data between communications hardware and main circuit board 200. In other embodiments, communications interface 222 may be a system on a chip (SOC) or other integrated system which allows for transmission of data and reception of data. In such a case, communications interface 222 may be coupled directly to main circuit board 200 as either a removable package or embedded package.

Some embodiments of portable ultrasound system 100 include power supply board 224. Power supply board 224 includes components and circuitry for delivering power to components and devices within and/or attached to portable ultrasound system 100. In some embodiments, power supply board 224 includes components for alternating current and direct current conversion, for transforming voltage, for delivering a steady power supply, etc. These components may include transformers, capacitors, modulators, etc. to perform the above functions. In further embodiments, power supply board 224 includes circuitry for determining the available power of a battery power source. In other embodiments, power supply board 224 may receive information regarding the available power of a battery power source from circuitry located remote from power supply board 224. For example, this circuitry may be included within a battery. In some embodiments, power supply board 224 includes circuitry for switching between power sources. For example, power supply board 224 may draw power from a backup battery while a main battery is switched. In further embodiments, power supply board 224 includes circuitry to operate as an uninterruptable power supply in conjunction with a backup battery. Power supply board 224 also includes a connection to main circuit board 200. This connection may allow power supply board 224 to send and receive information from main circuit board 200. For example, power supply board 224 may send information to main circuit board 200 allowing for the determination of remaining battery power. The connection to main circuit board 200 may also allow main circuit board 200 to send commands to power supply board 224. For example, main circuit board 200 may send a command to power supply board 224 to switch from one source of power to another (e.g., to switch to a backup battery while a main battery is switched). In some embodiments, power supply board 224 is configured to be a module. In such cases, power supply board 224 may be configured so as to be a replaceable and/or upgradable module. In some embodiments, power supply board 224 is or includes a power supply unit. The power supply unit may convert AC power to DC power for use in portable ultrasound system 100. The power supply may perform additional functions such as short circuit protection, overload protection, undervoltage protection, etc. The power supply may conform to ATX specification. In other embodiments, one or more of the above described functions may be carried out by main circuit board 200.

Main circuit board 200 may also include power supply interface 226 which facilitates the above described communication between power supply board 224 and main circuit board 200. Power supply interface 226 may include connections which enable communication between components of main circuit board 200 and power supply board 224. In further embodiments, power supply interface 226 includes additional circuitry to support the functionality of power supply board 224. For example, power supply interface 226 may include circuitry to facilitate the calculation of remaining battery power, manage switching between available power sources, etc. In other embodiments, the above described functions of power supply board 224 may be carried out by power supply interface 226. For example, power supply interface 226 may be a SOC or other integrated system. In such a case, power supply interface 226 may be coupled directly to main circuit board 200 as either a removable package or embedded package.

With continued reference to FIG. 2, some embodiments of main circuit board 200 include user input interface 228. User input interface 228 may include connections which enable communication between components of main circuit board 200 and user input device hardware. For example, user input interface 228 may provide a connection between main circuit board 200 and a capacitive touchscreen, resistive touchscreen, mouse, keyboard, buttons, and/or a controller for the proceeding. In one embodiment, user input interface 228 couples controllers for touchpad 170, touchscreen 172, and main screen 190 to main circuit board 200. In other embodiments, user input interface 228 includes controller circuitry for touchpad 170, touchscreen 172, and main screen 190. In some embodiments, main circuit board 200 includes a plurality of user input interfaces 228. For example, each user input interface 228 may be associated with a single input device (e.g., touchpad 170, touchscreen 172, a keyboard, buttons, etc.).

In further embodiments, user input interface 228 may include additional circuitry to support the functionality of attached user input hardware or to facilitate the transfer of data between user input hardware and main circuit board 200. For example, user input interface 228 may include controller circuitry so as to function as a touchscreen controller. User input interface 228 may also include circuitry for controlling haptic feedback devices associated with user input hardware. In other embodiments, user input interface 228 may be a SOC or other integrated system which allows for receiving user inputs or otherwise controlling user input hardware. In such a case, user input interface 228 may be coupled directly to main circuit board 200 as either a removable package or embedded package.

Main circuit board 200 may also include ultrasound board interface 230 which facilitates communication between ultrasound board 232 and main circuit board 200. Ultrasound board interface 230 may include connections which enable communication between components of main circuit board 200 and ultrasound board 232. In further embodiments, ultrasound board interface 230 includes additional circuitry to support the functionality of ultrasound board 232. For example, ultrasound board interface 230 may include circuitry to facilitate the calculation of parameters used in generating an image from ultrasound data provided by ultrasound board 232. In some embodiments, ultrasound board interface 230 is a SOC or other integrated system. In such a case, ultrasound board interface 230 may be coupled directly to main circuit board 200 as either a removable package or embedded package.

In other embodiments, ultrasound board interface 230 includes connections which facilitate use of a modular ultrasound board 232. Ultrasound board 232 may be a module (e.g., ultrasound module) capable of performing functions related to ultrasound imaging (e.g., multiplexing sensor signals from an ultrasound probe/transducer, controlling the frequency of ultrasonic waves produced by an ultrasound probe/transducer, etc.). The connections of ultrasound board interface 230 may facilitate replacement of ultrasound board 232 (e.g., to replace ultrasound board 232 with an upgraded board or a board for a different application). For example, ultrasound board interface 230 may include connections which assist in accurately aligning ultrasound board 232 and/or reducing the likelihood of damage to ultrasound board 232 during removal and/or attachment (e.g., by reducing the force required to connect and/or remove the board, by assisting, with a mechanical advantage, the connection and/or removal of the board, etc.).

In embodiments of portable ultrasound system 100 including ultrasound board 232, ultrasound board 232 includes components and circuitry for supporting ultrasound imaging functions of portable ultrasound system 100. In some embodiments, ultrasound board 232 includes integrated circuits, processors, and memory. Ultrasound board 232 may also include one or more transducer/probe socket interfaces 238. Transducer/probe socket interface 238 enables ultrasound transducer/probe 234 (e.g., a probe with a socket type connector) to interface with ultrasound board 232. For example, transducer/probe socket interface 238 may include circuitry and/or hardware connecting ultrasound transducer/probe 234 to ultrasound board 232 for the transfer of electrical power and/or data. Transducer/probe socket interface 238 may include hardware which locks ultrasound transducer/probe 234 into place (e.g., a slot which accepts a pin on ultrasound transducer/probe 234 when ultrasound transducer/probe 234 is rotated). In some embodiments, ultrasound board 232 includes two transducer/probe socket interfaces 238 to allow the connection of two socket type ultrasound transducers/probes 187.

In some embodiments, ultrasound board 232 also includes one or more transducer/probe pin interfaces 236. Transducer/probe pin interface 236 enables an ultrasound transducer/probe 234 with a pin type connector to interface with ultrasound board 232. Transducer/probe pin interface 236 may include circuitry and/or hardware connecting ultrasound transducer/probe 234 to ultrasound board 232 for the transfer of electrical power and/or data. Transducer/probe pin interface 236 may include hardware which locks ultrasound transducer/probe 234 into place. In some embodiments, ultrasound transducer/probe 234 is locked into place with locking lever system 120. In some embodiments, ultrasound board 232 includes more than one transducer/probe pin interfaces 236 to allow the connection of two or more pin type ultrasound transducers/probes 234. In such cases, portable ultrasound system 100 may include one or more locking lever systems 120. In further embodiments, ultrasound board 232 may include interfaces for additional types of transducer/probe connections.

With continued reference to FIG. 2, some embodiments of main circuit board 200 include display interface 240. Display interface 240 may include connections which enable communication between components of main circuit board 200 and display device hardware. For example, display interface 240 may provide a connection between main circuit board 200 and a liquid crystal display, a plasma display, a cathode ray tube display, a light emitting diode display, and/or a display controller or graphics processing unit for the proceeding or other types of display hardware. In some embodiments, the connection of display hardware to main circuit board 200 by display interface 240 allows a processor or dedicated graphics processing unit on main circuit board 200 to control and/or send data to display hardware. Display interface 240 may be configured to send display data to display device hardware in order to produce an image. In some embodiments, main circuit board 200 includes multiple display interfaces 240 for multiple display devices (e.g., three display interfaces 240 connect three displays to main circuit board 200). In other embodiments, one display interface 240 may connect and/or support multiple displays. In one embodiment, three display interfaces 240 couple touchpad 170, touchscreen 172, and main screen 190 to main circuit board 200.

In further embodiments, display interface 240 may include additional circuitry to support the functionality of attached display hardware or to facilitate the transfer of data between display hardware and main circuit board 200. For example, display interface 240 may include controller circuitry, a graphics processing unit, video display controller, etc. In some embodiments, display interface 240 may be a SOC or other integrated system which allows for displaying images with display hardware or otherwise controlling display hardware. Display interface 240 may be coupled directly to main circuit board 200 as either a removable package or embedded package. Processing circuit 210 in conjunction with one or more display interfaces 240 may display images on one or more of touchpad 170, touchscreen 172, and main screen 190.

Referring back to FIG. 1A, in some embodiments, portable ultrasound system 100 includes one or more pin type ultrasound probe interfaces 122. Pin type ultrasound interface 122 may allow an ultrasound probe to connect to an ultrasound board 232 included in ultrasound system 100. For example, an ultrasound probe connected to pin type ultrasound interface 122 may be connected to ultrasound board 232 via transducer/probe pin interface 236. In some embodiments, pin type ultrasound interface 122 allows communication between components of portable ultrasound system 100 and an ultrasound probe. For example, control signals may be provided to the ultrasound probe 112 (e.g., controlling the ultrasound emissions of the probe) and data may be received by ultrasound system 100 from the probe (e.g., imaging data).

In some embodiments, ultrasound system 100 may include locking lever system 120 for securing an ultrasound probe. For example, an ultrasound probe may be secured in pin type ultrasound probe interface 122 by locking lever system 120.

In further embodiments, ultrasound system 100 includes one or more socket type ultrasound probe interfaces 124. Socket type ultrasound probe interfaces 124 may allow a socket type ultrasound probe to connect to an ultrasound board 232 included in ultrasound system 100. For example, an ultrasound probe connected to socket type ultrasound probe interface 124 may be connected to ultrasound board 232 via transducer/probe socket interface 238. In some embodiments, socket type ultrasound probe interface 124 allows communication between components of portable ultrasound system 100 and other components included in or connected with portable ultrasound system 100. For example, control signals may be provided to an ultrasound probe (e.g., controlling the ultrasound emissions of the probe) and data may be received by ultrasound system 100 from the probe (e.g., imaging data).

Figure 3:
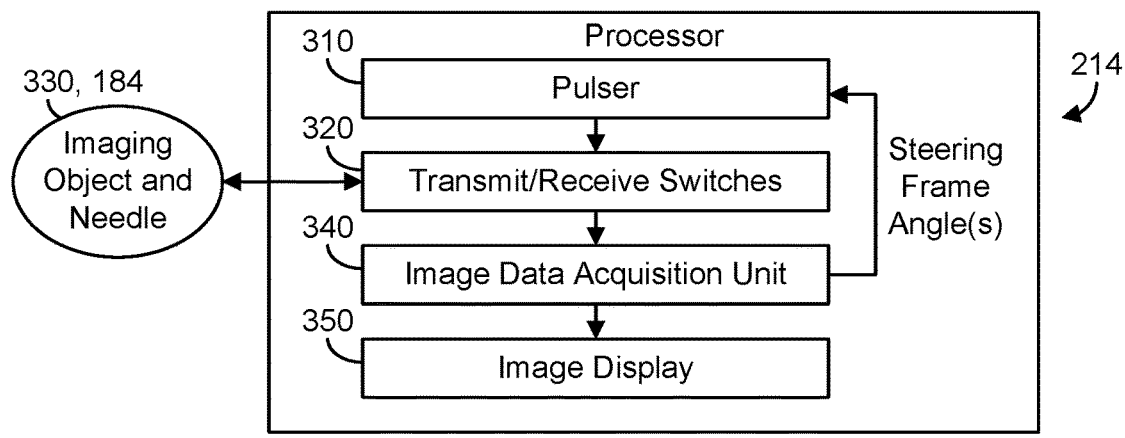
FIG. 3 is a block diagram illustrating a processor of the portable ultrasound system of FIG. 2.

Referring now to FIG. 3, a block diagram illustrating processor 214 is shown, according to an exemplary embodiment. Processor 214 may include a pulser 310, transmit/receive switches 320, an image data acquisition unit 340, and an image display 350 and communicates with an imaging object 330 and needle 184.

Pulser 310 provides the electrical voltage required for excitation of the piezoelectric transducer elements in transducer assembly 102. Pulser 310 may control the output transmit power by adjusting the electrical voltage. In a system that includes a beamformer, the amplitude of the voltage output by pulser 310 may be determined by a digital to analog converter. If the amplitude of the voltage output by pulser 310 is increased, the ultrasound waves transmitted have a higher intensity and echo detection from weaker reflectors may be improved. In another embodiment, the pulser 310 may have a low power setting for obstetric imaging to reduce the power deposited into a fetus.

Transmit/receive switches 320 may be synchronized with pulser 310. The transmit/receive switches 320 may be configured to isolate high voltage associated with pulsing from sensitive amplification stages during the receive mode. The receive mode collects the induced voltages caused by the returning echoes, which consist of a much lower amplitude than the voltages for transmission.

Imaging object 330 and needle 184 may be a patient, a phantom, or other object to receive imaging, with a needle. The imaging for the patient may take place for diagnostic examination (e.g., an abdominal, an obstetric and gynecological, a cardiac, a pediatric, a musculoskeletal, etc.), research or training. The needle 184 placement may be not yet entered the imaging object 330, partially inserted into imaging object 330, or fully inserted into imaging object 330.

Image data acquisition unit 340 is discussed in detail with reference to FIG. 4.

Image display 350 receives information from a scan converter and projects the image onto main screen 190. Once the image is displayed, the user input interface 228 may be used to make adjustments to the image to improve image quality. The quality and resolution of the image may be limited by the main screen 190 settings. Zoom features may be available to improve the image being displayed. Two types of zoom features that are commonly used are "read" and "write" zoom. Read zoom enlarges a user defined region of the image and expands the stored information over a larger number of pixels. While the image gets enlarged, the resolution does not change. In contrast, write zoom requires the selected area to be rescanned. The transducer assembly 102 only scans the selected area, and only echoes within the region are acquired.

Figure 4:
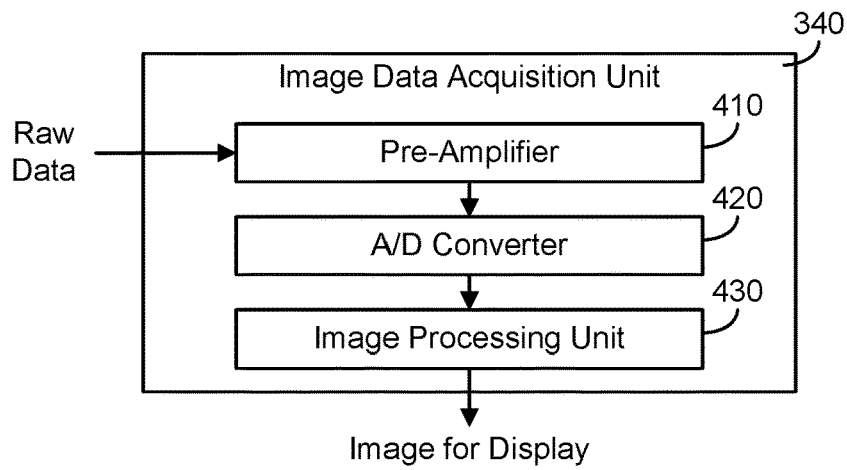
FIG. 4 is a block diagram illustrating an image data acquisition unit of the processor of FIG. 3, according to an exemplary embodiment.

Referring now to FIG. 4, a block diagram illustrating image data acquisition unit 340 of the processor 214 is shown, according to an exemplary embodiment. Pre-amplifier 410 may receive the detected signal voltages from the raw ultrasound data, and amplifies the voltages to useful signal levels. In another embodiment, each piezoelectric element in the ultrasound assembly 100 has its own pre-amplifier 410. The amplified data may be transmitted to the analog to digital (A/D) converter 420, which takes the analog data and coverts it to digital data. In another embodiment, each piezoelectric element in the ultrasound assembly 100 has its own A/D converter 420. In other embodiments, the per-amplifier 410 and A/D converter 420 can run in parallel. The A/D converter 420 may transmit the digital data to the imaging processing unit 430, which is discussed in detail in regard to FIG. 5.

Figure 5:
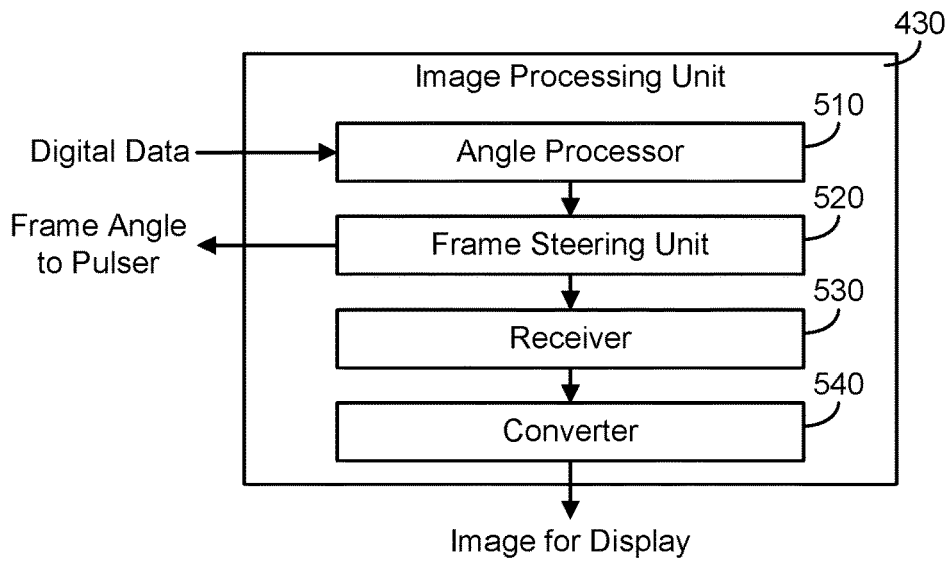
FIG. 5 is a block diagram illustrating an image processing unit of the image data acquisition unit of FIG. 4, according to an exemplary embodiment.

Referring now to FIG. 5, a block diagram illustrating image processing unit 430 of the image data acquisition unit 340 is shown, according to an exemplary embodiment. The digital data transmitted from A/D converter 420 is received by an angle processor 510, which will be discussed in detail with regard to FIGS. 6A-6B. The processed channel data may be transmitted to a frame steering unit 520.

Frame steering unit 520 may generate the electronic delay for individual transducer elements in an array. This causes transmit and receiving focus, which, in a phased array, causes beam steering to occur. In another embodiment, the frame steering unit 520 may be a beamformer. The frame steering unit 520 may be a digital beamformer.

Receiver 530 may receive data from the frame steering unit 520, which may represent echo information as a function of time, which corresponds to depth. The receiver 530 may be configured to conduct further processing. The processing done by the receiver 530 may include gain adjustments and dynamic frequency tuning, dynamic range compression, rectification, demodulation, and envelope detection, rejection, and processed images.

Gain adjustments may be user-adjustable amplification settings for the returning echo signals as a function of time, which further compensates for beam attenuation. Gain adjustments may be varied based on the particular application of the ultrasound system 100. In general, the ideal gain adjustments make all equally reflective boundaries equal amplitude, regardless of the depth.

Dynamic frequency tuning involves changing the sensitivity of a tuner bandwidth with time. This may result in echoes from shallower depths to be tuned to a higher frequency. In another embodiment, echoes from a deeper depths are tuned to a lower frequency. Dynamic frequency tuning may accommodate for the increased attenuation with respect to depth.

Dynamic range compression defines the operational range of an electronic device from a threshold level to a saturation level. Signal ranges may be reduced to allow accurate display images. In some embodiments, the dynamic range compression is done in analog. In other embodiments, the dynamic range compression is done in digital.

Rectification inverts negative echo signals to positive echo signals. Demodulation and envelope detection convert rectified amplitudes into a smoothed, single pulse. Rejection may allow for thresholds to be set by the user for digitizing. Only signal data with amplitudes higher than the threshold will be digitized. This removes low-level noise and sound scattered by the electronics. Processed images are optimized for gray-scale or color ranges so no further adjustments are needed. The receiver 530 may transmit the processed data to converter 540.

Converter 540 creates the image from the echo information from distinct beam directions. The converter 540 may also perform scan conversion which enables the image data to be viewed on main screen 190 because the image acquisition and display may have different formats. In some embodiments, digital data from the converter 540 is transmitted to a scan converter memory. The scan converter memory may be configured as a matrix, where each pixel has a memory address that distinctly distinguishes its location. During image acquisition, the digital signals are placed into the memory address that corresponds to the relative reflector position in the transducer probe 112, as close as possible. The transducer beam, orientation, and echo delay times may determine the memory address where the information may be stored. Converter 540 may transmit the data for the image display.

Figure 6A:
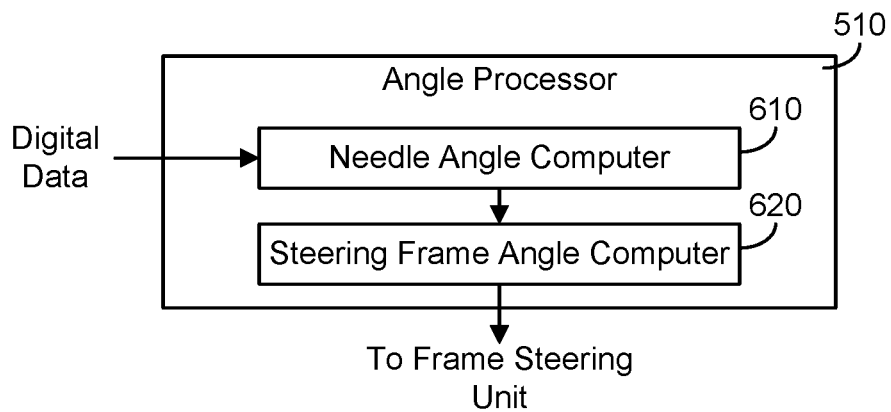
FIG. 6A-6B are block diagrams illustrating an angle processor of the image processing unit of FIG. 5 in greater detail, according to an exemplary embodiment.

Referring to FIG. 6A, a block diagram illustrating an angle processor of the image processing 430 unit of FIG. 5 is shown in greater detail, according to an exemplary embodiment. The angle processor 510 may receive digital data. The digital data may be from A/D converter 420. The angle processor 510 includes a needle angle computer 610 and a steering frame angle computer 620. The digital data may be received by the needle angle computer 610. Needle angle computer 610 computes the angle of needle 184. The needle angle computer 610 may subtract a tissue frame from a steered frame. In another embodiment, the needle angle computer 610 may use edge detection processing to remove grating lobes. In other embodiments, the needle angle computer 610 may utilize other imaging techniques to identify the angle of the needle 184. In another embodiment, needle angle computer 610 may perform a combination of techniques for computing the angle of needle 184.

The steering frame angle computer 620 determines the steering frame angle to be used for subsequent firings from the transducer assembly 102. The steering frame angle computer 620 may determine the steering frame angle by identifying the angle of the frame that has the highest energy. The steering frame computer 620 may transmit the steering frame angles to the frame steering unit 520. The steering frame angles may be used for more selective areas for subsequent firings.

Figure 6B:
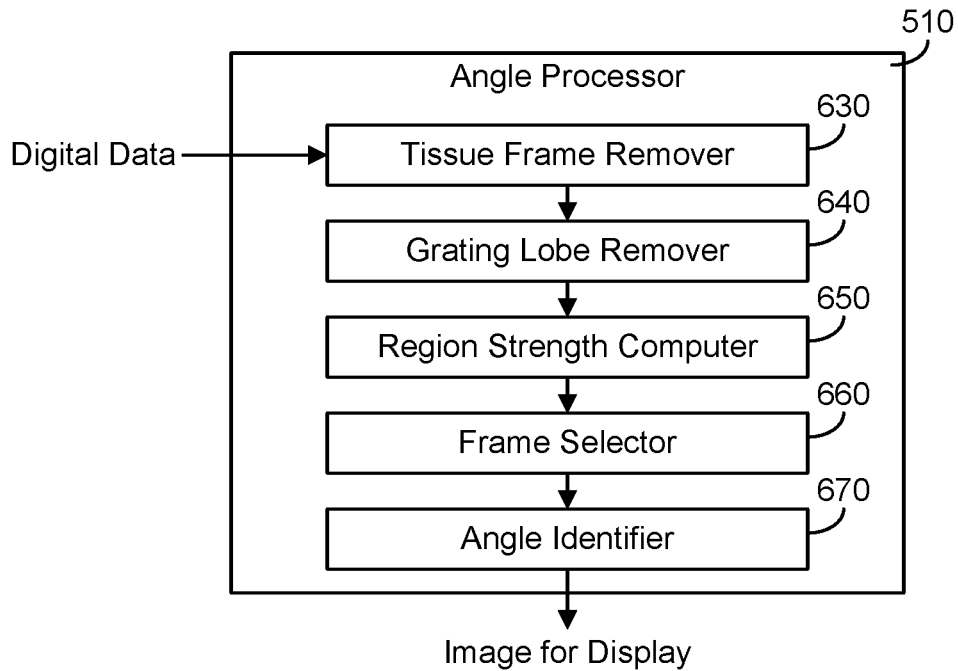

Referring to FIG. 6B, a more detailed block diagram illustrating an angle processor 510 of the image processing unit 430 of FIG. 5 is shown, according to an exemplary embodiment. Angle processor 510 includes a tissue frame remover 630, a grating lobe remover 640, a region strength computer 650, a frame selector 660, and an angle identifier 670. Tissue frame remover 630 may receive imaging data. In another embodiment, tissue frame remover 630 receives digital data. In other embodiments, the data received by tissue frame remover 630 is received from A/D converter 420. The data received by tissue frame remover 630 may include data separated by frame steering angle. The tissue frame remover 630 may subtract or remove a tissue frame angle from a needle frame angle. In one embodiment, the tissue frame angle may be a zero angle transmission from transducer probe 112. In another embodiment, the needle frame angle is a nonzero angle transmission from transducer probe 112. In other embodiments, the needle frame angle is a combination of frame angle transmissions from transducer probe 112. The tissue frame remover 630 may transmit the processed imaging data to grating lobe remover 640.

Grating lobe remover 640 removes the grating lobes from the imaging data received from tissue frame remover 630. The grating lobe remover 640 may use edge detection processing to remove the grating lobes. Grating lobe remover 640 may utilize other imaging techniques for grating lobe removal. Grating lobe remover 640 transmits the imaging data to the region strength computer 650.

The region strength computer 650 computes the total strength of the returned energy in the region of interest. The region strength computer 650 may use a summing device to determine the total strength. The region strength computer 650 region of interest may be the entire region scanned. In another embodiment, the region of interest may be a partial section of the scanned image. In one embodiment, the region of interest may be user defined. In another embodiment, the region of interest is determined based on the data. The region strength computer 650 transmits to the frame selector 660.

The frame selector 660 may select the frame for subsequent firings. In some embodiments, the frame selector 660 selects multiple frames for subsequent firings. In another embodiment, the frame selector 660 selects the frame with the highest strength. The frame selector 660 transmits the data to an angle identifier 670.

Angle identifier 670 identifies the angle of the frame or frames that were selected by the frame selector 660. The angle identifier 670 transmits the data to the frame steering unit 520. The angle identifier 670 may identify the frame angle using a statistical function (e.g. max). In other embodiments, the needle angle is identified using image transformations.

Still referring to FIG. 6B, the angle processor 510 may adaptively change the steering frame angle based on changes in the needle angle. In other embodiments, the angle processor 510 changes the steering frame periodically. In another embodiment, the angle processor 510 the steering frame angle is changed continuously.

Referring in general to the first set of firings in FIG. 6A-6B, transmitting low density firings can require complex scanning control architecture where the number and type of transmit firings can be configured for every frame. In another embodiment, sparse firings are used on a periodic basis (e.g. once every second) for coarse angle identification. In one embodiment, the first set of firings are triggered by an event (e.g. needle entrance). Such an implementation may be preferred for simpler interrupt driven architectures where the low-density firings are treated like mixed-modes (e.g. color Doppler or spectral Doppler).

Referring in general to the angle computer in FIG. 6A-6B, other methods that utilize morphological or structural information or information about the needle targets can be utilized to compute the needle angle. Some standard image segmentation methods such as region identification and labelling can be used for isolating the needle from the rest of the image. The needle angle may be identified using simple regression analysis or using image transformations such as Hough transformations.

Figure 7:
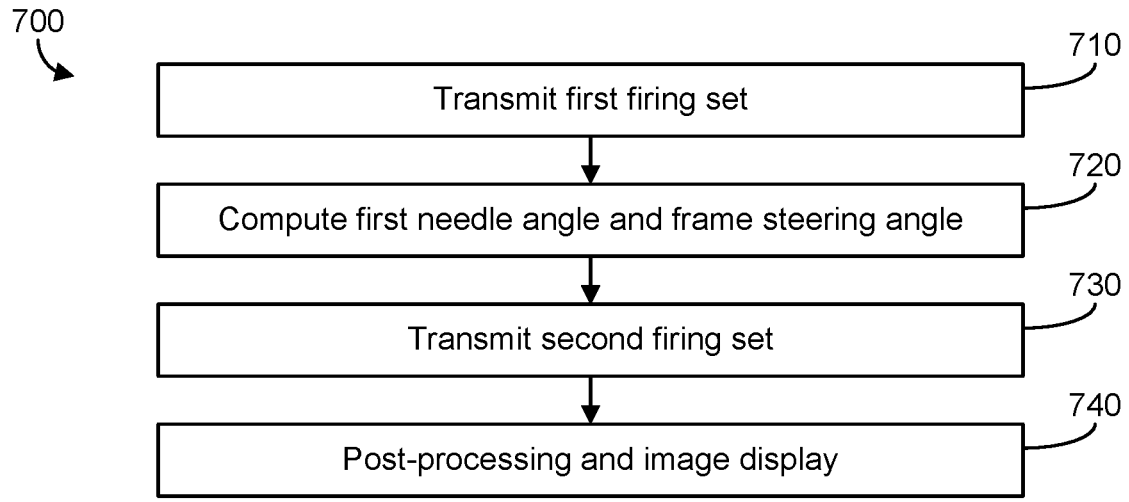
FIG. 7 is a flowchart of a process for processing steering frame angle adjustment in an ultrasound system, according to an exemplary embodiment.

FIG. 7 is a flowchart of a process 700 for processing steering frame angle adjustment in an ultrasound system, according to an exemplary embodiment. The process 700 begins with transmitting a first set of firings 710. The ultrasound probe 112 fires a first set of sound waves. In one embodiment, the first firings are coarse firings. In another embodiment, low density firings are transmitted for the first set of firings 710. In one embodiment, sparse frames are used in a periodic basis. In another embodiment, multiple frame angles are involved in the transmit of the first set of firing 710. The first set of firings 710 may be dense firings. In one embodiment, the first set of firings are triggered by an event (e.g. needle entrance).

The next step in process 700 is to compute a first needle angle and frame steering angle 720. In some embodiments, computing a first needle angle and frame steering angle 720 is performed by angle processor 510. In another embodiment, computing a first needle angle and frame steering angle 720 is performed by software of ultrasound system 100. Computing a first needle angle 720 may include subtracting a tissue frame from a steered frame. In another embodiment, computing a first needle angle 720 may use edge detection processing to remove grating lobes. In other embodiments, computing a first needle angle 720 may utilize other imaging techniques to identify the angle of the needle 184. In another embodiment, computing a first needle angle 720 may perform a combination of techniques for computing the angle of needle 184. Computing a first needle angle and frame steering angle 720 may involve determining the steering frame angle by identifying the angle of the frame that has the highest energy. The steering frame angles may be used for more selective areas for subsequent firings.

The next step of process 700 is to transmit a second firing set 730. Ultrasound probe 112 transmits a second set of firings. In one embodiment, the second of firings are coarse firings. In another embodiment, low density firings are transmitted for the second firing set 730. In another embodiment, multiple frame angles are involved in the transmitting of the second set of firings 730. In other embodiments, to transmit the second set of firings 730, dense firings are used. In another embodiment, the transmitting of the second set of firings 730 is configured for the identified first needle angle. In one embodiment, the first set of firings as triggered by an event (e.g. needle entrance).

The next step in process 700 is post-processing and image display 740. Post-processing and image display 740 utilizes the information from the transmitted second set of firings 730 to generate an image for display. In some embodiments, post-processing and image display 740 is done by receiver 530. In another embodiment, post-processing and image display 740 is done be converter 540. In yet another embodiment, post-processing and image display 740 is done by both receiver 530 and converter 540. In other embodiments, post-processing and image display 740 is done by software of ultrasound imaging system 100. Post-processing and image display 740 may include gain adjustments and dynamic frequency tuning, dynamic range compression, rectification, demodulation, and envelope detection, rejection, and processed images.

Gain adjustments may be user-adjustable amplification settings for the returning echo signals as a function of time, which further compensation for beam attenuation. Gain adjustments may be varied based on the particular application of the ultrasound system 100. In general, the ideal gain adjustments make all equally reflective boundaries equal amplitude, regardless of the depth.

Dynamic frequency tuning involves changing the sensitivity of a tuner bandwidth with time. This may result in echoes from shallower depths to be tuned to a higher frequency. In another embodiment, echoes from a deeper depths are tuned to a lower frequency. Dynamic frequency tuning is conducted to accommodate for the increased attenuation with respect to depth.

Dynamic range compression defines the operational range of an electronic device from a threshold level to a saturation level. Signal ranges may be reduced to allow accurate display images. In some embodiments, the dynamic range compression is done in analog. In other embodiments, the dynamic range compression is done in digital. Rectification inverts negative echo signals to positive echo signals. Demodulation and envelope detection convert rectified amplitudes into a smoothed, single pulse.

Rejection may allow for thresholds to be set by the user for digitizing. Only signal data with amplitudes higher than the threshold will be digitized. This removes low-level noise and sound scattered by the electronics. Processed images are optimized for gray-scale or color ranges so no further adjustments are needed.

Still referring to FIG. 7, post-processing and image display 740 creates the image from the echo information from distinct beam directions. The post-processing and image display 740 may also perform scan conversion which enables the image data to be viewed on video display 190 because the image acquisition and display may have different formats. In some embodiments, digital data from the post-processing and image display 740 is transmitted to a scan converter memory. The scan converter memory may be configured as a matrix, where each pixel has a memory address that distinctly distinguishes its location. During image acquisition, the digital signals are placed into the memory address that corresponds to the relative reflector position in the transducer probe 112, as close as possible. The transducer beam, orientation, and echo delay times may determine the memory address where the information may be stored. Post-processing and image display 740 may transmit the data for the image display. The image may be displayed on main screen 190.

Figure 8:
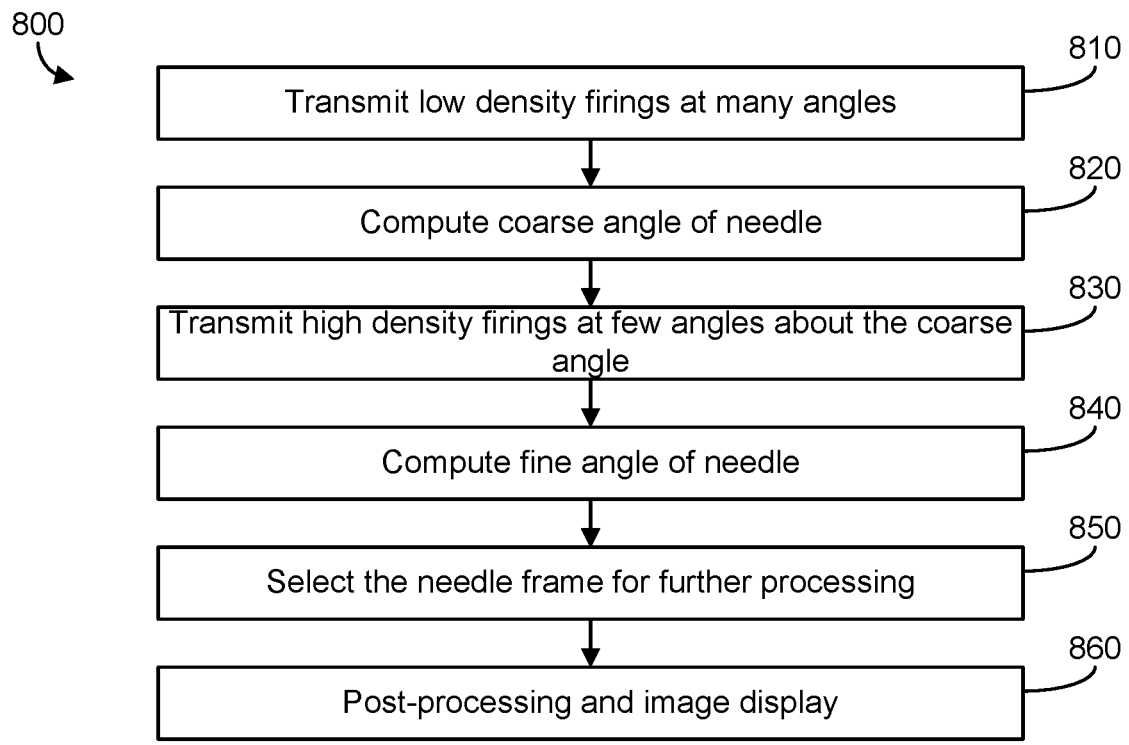
FIG. 8 is a flowchart of a process for processing steering frame angle adjustment in an ultrasound system, shown in greater detail, according to an exemplary embodiment.

FIG. 8 is a flowchart of a process 800 for processing steering frame angle adjustment in an ultrasound system 100, shown in greater detail, according to an exemplary embodiment. The process 800 beings with transmitting low density firings at many angles 810. The ultrasound probe 112 may be used to transmit low density firings at many angles 810.

The next step in process 800 is compute coarse angle of needle 820. The coarse angle of needle may be the angle of the needle 184 in respect to the ultrasound probe 112. In some embodiments, computing the coarse needle angle 820 is performed by angle processor 510. In another embodiment, computing the coarse needle angle 820 is performed by software of ultrasound system 100. Computing the coarse needle angle 820 may include subtracting a tissue frame from a steered frame. In another embodiment, computing the coarse needle angle 820 may use edge detection processing to remove grating lobes. In other embodiments, computing the coarse needle angle 820 may utilize other imaging techniques to identify the angle of the needle 184. In another embodiment, computing the coarse needle angle 820 may perform a combination of techniques for computing the angle of needle 184. In some embodiments, computing the coarse needle angle 820 may involve determining the steering frame angle. Determining the steering frame angle may be done by identifying the angle of the frame that has the highest energy. The steering frame angles may be used for more selective areas for subsequent firings.

The next step in process 800 is transmit high density firings at a few angles about the coarse angle 830. The coarse angle determined in step 820 is used to define a set of angles, about the coarse angle for subsequent firings. For example, if the angle is determined to be 50 degrees, dense firing may occur between 49 degrees and 51 degrees. The spread of the dense firings may be determined by the user. In another embodiment, the spread of the dense firings may be determined by the angle processor 510 through adaptive adjustment. For example, if the coarse set of firings cause a frame, with the highest energy, to have an energy higher than a certain threshold, the spread is smaller than if the frame, with the highest energy, is below the threshold.

The next step in process 800 is compute fine angle of needle 840. The fine angle of needle may be the angle of the needle 184 in respect to the ultrasound probe 112. In some embodiments, computing the fine needle angle 820 is performed by angle processor 510. In another embodiment, computing the fine needle angle 820 is performed by software of ultrasound system 100. The fine angle of the needle is computed the same way as the coarse needle angle of step 820.

The next step in process 800 is selecting the needle frame for further processing 850. The frame that is selected may be the frame with the highest energy. The frame with the highest energy may be determined using statistical function (e.g. max). In other embodiments, the needle frame is selected using image transformations. The frame with the highest energy may be determined using mathematical manipulation prior to a statistical function.

Another step in process 800 is post-processing and image display 860. This step is identical to step 740 in process 700, as described in respect to FIG. 7.

Figure 9:
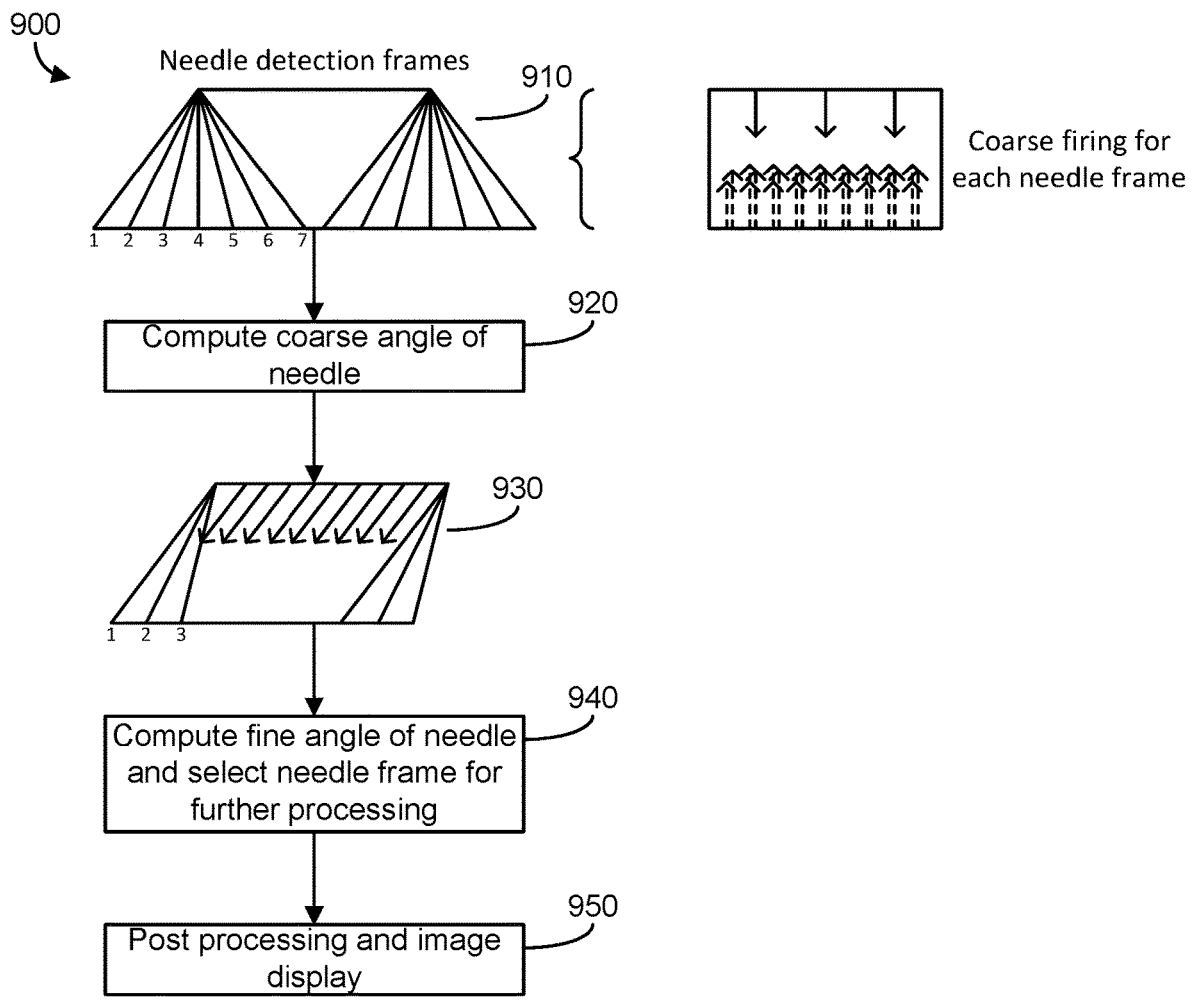
FIG. 9 is a flowchart of a process for processing steering frame angle adjustment in an ultrasound system, with drawings for greater detail and clarification, according to an exemplary embodiment.

FIG. 9 is a flowchart of a process 900 for processing steering frame angle adjustment in an ultrasound system, with drawings for greater detail and clarification, according to an exemplary embodiment. The first step is transmit low density firings at many angles 910. The coarse firings may be transmitted by ultrasound probe 112. Looking at the drawing relating to step 910, it can be seen that 7 angles are used in the firing. It should be noted that while 7 angles are used, this is just an example, and more or less angles may be used. Also looking at step 910 is the single frame angle view. Coarse firings may involve few firings per steering angle frame. The steering frame angle of zero degrees can be seen with three firings at this angle, in step 910 of process 900. It should be noted that this is just an example, and more or less firings may be used per frame angle.

The second step of process 900 is compute coarse angle of needle 920. This step is identical to step 820 in process 800, as described in respect to FIG. 8.

The third step of process 900 is transmit high density firings at few angles about the coarse angle 930. The dense firings may be transmitted by ultrasound probe 112. Looking at the drawing relating to step 930, it can be seen that 3 angles are used in the firing. It should be noted that while 3 angles are used, this is just an example, and more or less angles may be used. Also looking at step 930 is the firings per steering frame angle. Dense firings may involve many firings per steering angle frame. The third steering frame angle can be seen with twelve firings at this angle, in step 930 of process 900. It should be noted that this is just an example, and more or less firings may be used per frame angle.

The next step of process 900 is compute the fine angle of the needle and select needle frame for further processing 940. This step is identical to steps 840 and 850 in process 800, as described in respect to FIG. 8.

The final step of process 900 is post-processing and image display 950. This step is identical to step 860 in process 800, as described in respect to FIG. 8.

Figure 10:
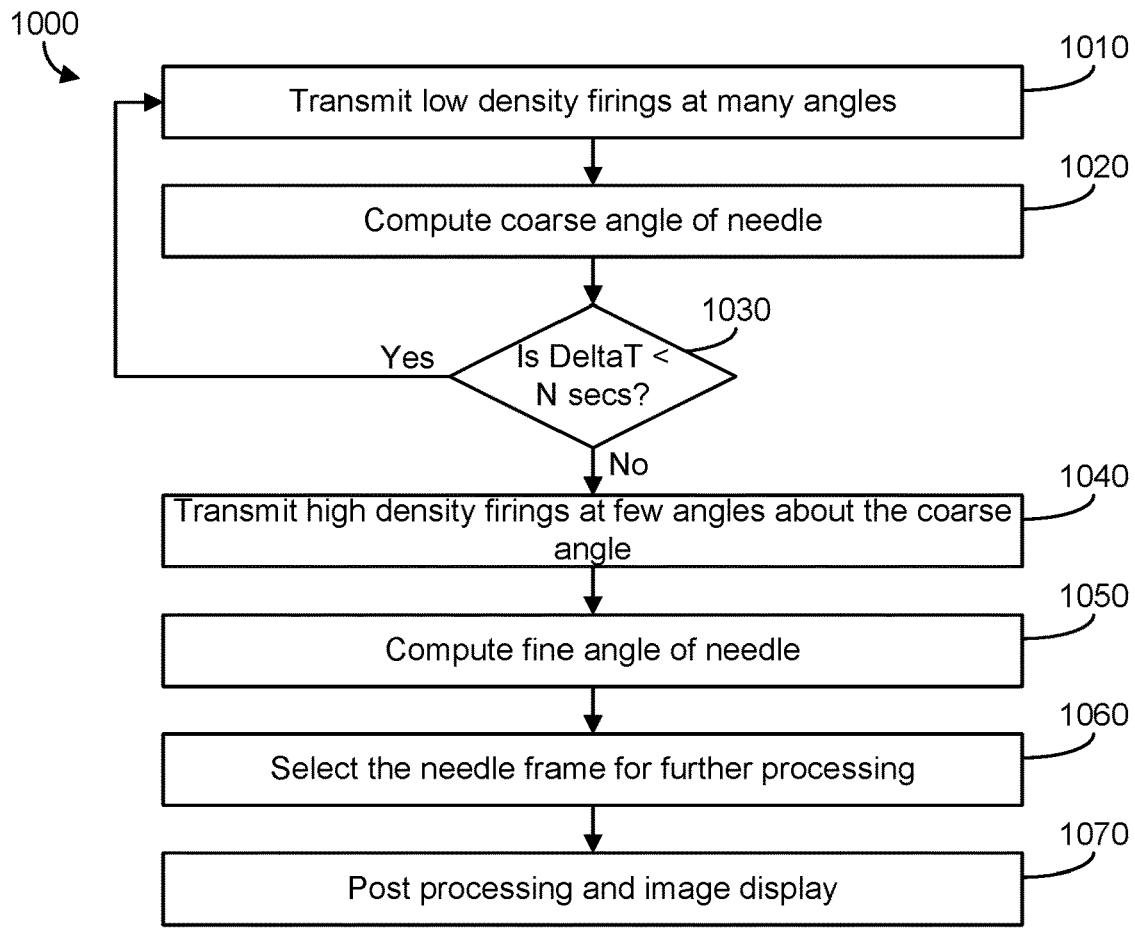
FIG. 10 is a flowchart of a process for processing steering frame angle adjustment in an ultrasound system, according to another embodiment.

FIG. 10 is a flowchart of a process 1000 for processing steering frame angle adjustment in an ultrasound system, according to another embodiment. One step is to transmit low density firings at many angles 1010. This step is identical to step 810 in process 800, as described in respect to FIG. 8. Another step is to compute a coarse angle of the needle 1020. This step is identical to step 820 in process 800, as described in respect to FIG. 8.

The next step in process 800 is to determine if DeltaT is less than N seconds 1030. DeltaT may be the time interval that has passed for the low density firings. For example, if each firing takes one second, and three firing sets have been made, DeltaT is three. N may be a user defined set of time that is desired to be reached before transmitting high density firings in step 1040. If the set of time has not been passed, the low density firings of step 1010 continue. Once the set of time has been passed, the system can move to step 1040.

Step 1040 is identical to step 830 in process 800, as described in respect to FIG. 8.

Step 1050 is identical to step 840 in process 800, as described in respect to FIG. 8.

Step 1060 is identical to step 850 in process 800, as described in respect to FIG. 8.

Step 1070 is identical to step 860 in process 800, as described in respect to FIG. 8.

Figure 11:
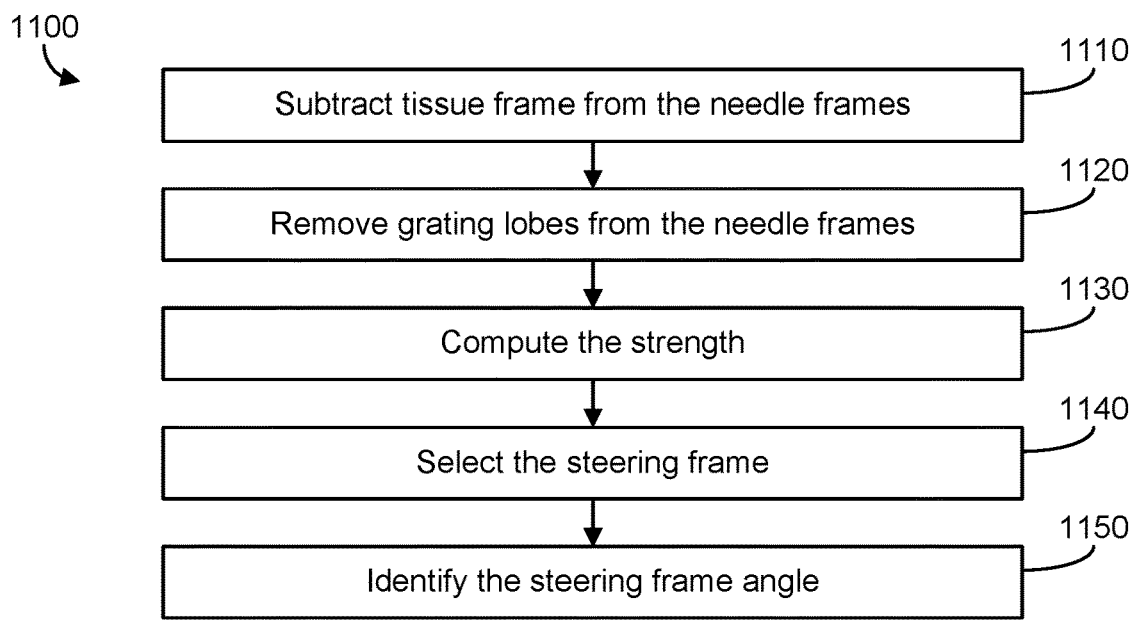
FIG. 11 is a flowchart of a process for computing needle angles and steering frame angles, according to an exemplary embodiment.

FIG. 11 is a flowchart of a process 1100 for computing needle angles and steering frame angles (i.e. step 820 in process 800 of FIG. 8), according to an exemplary embodiment. Process 1100 begins by subtracting tissue frame from the needle frames 1110. The tissue frame may be a frame where the tissue has the best visualization. In one embodiment, the tissue frame may be the steering frame with an angle of zero degrees. The needle frames may be the steering frames that are at nonzero angles. The tissue frame may be subtracted from each needle frames individually. In another embodiment, the tissue frame is subtracted from the combined needle frames.

The next step in process 1100 is removing grating lobes from the needle frames 1120. The grating lobes may be removed using edge processing methods. Removing grating lobes may utilize other imaging techniques for grating lobe removal.

The next step in process 1100 is computing the strength 1130. Computing the strength 1130 may involve computing the total strength. In another embodiment, computing the strength 1130 may involving summing the strengths. The strength may be computed for the entire region included in firing. In another embodiment, the strength may be computed only for a region of interest. In one embodiment, the region of interest is user defined. In another embodiment, the region of interest is defined as any frame with a strength above a certain threshold.

Another step in process 1100 is to select the steering frame 1140. The steering frame may be selected based on which frame has the highest strength. In one embodiment, the steering frame may be selected based on statistical functions. In other embodiments, the steering frame is selected using image transformations. The steering frame may be determined using mathematical manipulation prior to a statistical function.

Another step in process 1100 is identifying the steering frame angle 1150. Identifying the steering frame angle 1150 identifies the angle of the frame or frames that were selected by step 1140. Identifying the steering frame angle may identify the frame angle using a statistical function (e.g. max). In other embodiments, the needle angle is identified using image transformations.

Referring in general to the processes described in FIG. 7-11, transmitting low density firings can require complex scanning control architecture where the number and type of transmit firings can be configured for every frame. In another embodiment, sparse firings are used on a periodic basis (e.g. once every second) for coarse angle identification. In one embodiment, the first set of firings are triggered by an event (e.g. needle entrance). Such an implementation is preferred for simpler interrupt driven architectures where the low-density firings are treated like mixed-modes (e.g. color Doppler or spectral Doppler).

Referring in general to the processes described in FIG. 7-11, more specifically angle computation, other methods that utilize morphological or structural information or information about the needle targets can be utilized. Some standard image segmentation methods such as region identification and labelling can be used for isolating the needle from the rest of the image. The needle angle may be identified using simple regression analysis or using image transformations such as Hough transformations.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A needle visualization ultrasound system, comprising:
a needle;
an ultrasound interface that receives ultrasound imaging information from sets of firings; and
processing electronics coupled to the ultrasound interface and configured to:
identify, from ultrasound imaging information from a first set of firings, a first needle angle and a first steering frame angle, the first set of firings having a first density defined by a first number of firings per steering angle;
generate instructions to cause a second set of firings to be outputted based on the identified first needle angle and the identified first steering frame angle, the second set of firings having a second density defined by a second number of firings per steering angle greater than the first number of firings per steering angle, the second set of firings located about the identified first needle angle, the second set of firings comprising at least one firing steered at an angle less than the identified first needle angle and at least one firing steered at an angle greater than the identified first needle angle;
identify, from ultrasound imaging information from the second set of firings, a second needle angle and a second steering frame angle; and
generate an ultrasound image using the second needle angle and second steering frame angle.

2. The needle visualization ultrasound system of claim 1, wherein the first set of firings is triggered by an event.

3. The needle visualization ultrasound system of claim wherein the first set of firings is triggered by entrance of the needle.

4. The needle visualization ultrasound system of claim 1, wherein the processing electronics identify the first needle angle by subtracting a tissue frame from a steered frame, the tissue frame being obtained from the first set of firings.

5. The needle visualization ultrasound system of claim 1, wherein the processing electronics identify the first needle angle by removing grating lobes of the ultrasound imaging information through edge detection processing.

6. The needle visualization ultrasound system of claim 1, wherein the processing electronics identify the first needle angle using a statistical function.

7. The needle visualization ultrasound system of claim 1, wherein the processing electronics identify the first needle angle using an image transformation of the ultrasound imaging information.

8. The needle visualization ultrasound system of claim 1, wherein the processing electronics identify the first steering frame angle by identifying a steered frame with a highest energy.

9. The needle visualization ultrasound system of claim 1, wherein the processing electronics change a steering frame dynamically and adaptively to accommodate changes in an angle of the needle to enhance needle visualization.

10. The needle visualization ultrasound system of claim 9, wherein the change of the steering frame is made periodically.

11. The needle visualization ultrasound system of claim 9, wherein the change of the steering frame is made continuously.

12. The needle visualization ultrasound system of claim 1, wherein the processing electronics generate the instructions such that the second set of firings do not occur until a set time interval is reached.

13. An ultrasound machine comprising:
an ultrasound interface that receives ultrasound imaging information from multiple sets of firings to obtain steered frames; and
processing electronics coupled to the ultrasound interface and configured to utilize the ultrasound imaging information from the multiple sets of firings to identify the angle of a needle dynamically and adaptively, wherein the processing electronics are configured to:
receive an indication of entrance of the needle;
responsive to receiving the indication of the entrance of the needle, cause a first set of firings of the multiple sets of firings to be outputted, the first set of firings having a first density defined by a first number of firings per steering angle;
identify a first needle angle based on the first set of firings;
cause a second set of firings of the multiple sets of firings to be outputted with a second density defined by a second number of firings per steering angle greater than the first number of firings per steering angle, the second set of firings located about the identified first needle angle, the second set of firings comprising at least one firing steered at an angle less than the identified first needle angle and at least one firing steered at an angle greater than the identified first needle angle;
identify a second needle angle based on the second set of firings; and
generate an ultrasound frame using the identified second needle angle.

14. A method of steering adjustment for visualization of a needle, the method comprising:
receiving ultrasound imaging data from a first set of firings having a first density defined by a first number of firings per steering angle;
identifying a first needle angle based on the first set of firings;
determining a first steering angle based on the first set of firings;
providing instructions to output a second set of firings having a second density defined by a second number of firings per steering angle greater than the first number of firings per steering angle, the second set of firings located about the first needle angle, the second set of firings comprising at least one firing steered at an angle less than the identified first needle angle and at least one firing steered at an angle greater than the identified first needle angler;
receiving ultrasound imaging data from the second set of firings;

identifying a second needle angle based on the second set of firings;
determining a second steering angle based on the second set of firings;
generating an ultrasound image by processing the ultrasound imaging data from the second set of firings using the second needle angle and second steering angle and
adaptively and dynamically repeating the method to accommodate for needle angle.

15. The method of claim 14, wherein identifying the first needle angle involves subtracting a tissue frame of the ultrasound imaging data from steered frames of the first set of firings, the tissue frame being obtained from the first set of firings.

16. The method of claim 14, wherein identifying the first needle angle involves removing grating lobes of the ultrasound imaging data through edge detection processing.

17. The method of claim 14, wherein identifying the first needle angle involves using a statistical function.

18. The method of claim 14, wherein identifying the first needle angle involves using an image transformation of the ultrasound imaging data.

* * * * *